(12) United States Patent
Hjertman et al.

(10) Patent No.: US 7,473,241 B2
(45) Date of Patent: Jan. 6, 2009

(54) DEVICE AND METHOD FOR INJECTING

(75) Inventors: Birger Hjertman, Hässelby (SE); Frank Schiffmann, Burgdorf (CH)

(73) Assignee: Tecpharma Licensing AG, Burgdorf (CH)

( * ) Notice: Subject to any disclaimer, the term of this patent is extended or adjusted under 35 U.S.C. 154(b) by 1117 days.

(21) Appl. No.: 10/739,416

(22) Filed: Dec. 18, 2003

(65) Prior Publication Data
US 2004/0133150 A1    Jul. 8, 2004

Related U.S. Application Data

(63) Continuation of application No. PCT/CH02/00314, filed on Jun. 12, 2002.

(30) Foreign Application Priority Data
Jun. 20, 2001    (DE) ................................ 101 29 583

(51) Int. Cl.
*A61M 5/30*    (2006.01)
(52) U.S. Cl. ...................................................... 604/68
(58) Field of Classification Search ................ 604/511, 604/68, 135, 69, 70, 71, 72, 73, 131, 140–145, 604/187
See application file for complete search history.

(56) References Cited

U.S. PATENT DOCUMENTS

| 5,062,830 A | 11/1991 | Dunlap |
| 5,879,327 A | 3/1999 | Moreau DeFarges |
| 5,919,159 A | 7/1999 | Lilley et al. |
| 5,954,689 A | 9/1999 | Poulsen |

FOREIGN PATENT DOCUMENTS

| WO | WO 96/24398 | 8/1996 |
| WO | WO 00/10630 | 3/2000 |

*Primary Examiner*—Manuel A Mendez
(74) *Attorney, Agent, or Firm*—Dorsey & Whitney LLP

(57) ABSTRACT

The invention relates to a device for injecting a fluid including a pressure chamber for accommodating the fluid, a piston for expelling the fluid from the pressure chamber, a pressure mechanism for generating an expelling impulse or force, and a transfer body coupled to the pressure mechanism, wherein, in an initial position the transfer body is arranged at a distance away from a contact point for transferring a force or impulse onto the piston. The invention encompasses a method for injecting a fluid wherein a transfer body is freely accelerated for a distance and strikes a contact point thus generating an initial impulse or pressure to expel the fluid.

16 Claims, 5 Drawing Sheets

DEVICE AND METHOD FOR INJECTING

CROSS-REFERENCE TO RELATED APPLICATION(S)

This application is a Continuation of International Application No. PCT/CH02/00314, filed on Jun. 12, 2002, which claims priority to German Application No. 10129583.9, filed on Jun. 20, 2001, the contents of both are incorporated herein in their entirety.

BACKGROUND

The present invention relates to devices and methods for administering or injecting a substance, in particular for injecting a fluid or liquid such as a solution containing insulin.

Generally speaking, the present invention can be employed in a number of devices and methods in which it is necessary to put a substance, e.g., a fluid, under substantial pressure in order to expel it from a pressure chamber. The fluid can be a liquid or an oil, a jelly or any other substance. It is equally possible to use a powder or other substance made from solids. In the following, by way of example, reference will always be made to a fluid.

Devices are known in which a liquid to be injected is introduced into a pressure chamber and then expelled at high pressure due to a continuously applied spring force, in order to inject said liquid into the tissue of a human or animal.

SUMMARY

It is an object of the present invention to provide a device and a method for injecting a fluid, using which a freely selectable dosage can be dispensed under defined conditions, in particular with a pre-set pressure progression.

The device in accordance with one embodiment of the present invention comprises a pressure chamber for accommodating a fluid, comprising at least one opening, the pressure chamber preferably being formed such that the fluid in the pressure chamber can be supplied from a fluid reservoir. Furthermore, a piston is provided which can be moved in the pressure chamber and serves to expel the fluid from the pressure chamber. To this end, the fluid chamber is preferably designed cylindrically, wherein the piston, which provides a lateral seal, can be moved in the axial direction of the pressure chamber so as to expel the fluid through an opening in the pressure chamber. A pressure mechanism, such as a spring or a mechanism which can expel gas or a liquid at high pressure, serves to generate an expelling force or impulse for the fluid. In accordance with the invention, a force or impulse transfer body is coupled to said pressure mechanism, wherein in an initial position, i.e., before beginning to expel or inject the fluid, said force or impulse transfer body is arranged at a distance D away from a contact point for transferring a force or impulse onto the piston to expel the fluid. The contact point for transferring the force or impulse onto the piston can be directly on the piston itself or can be formed by a device connected to the piston.

In one embodiment, to initiate an injection, the pressure mechanism is triggered and causes the transfer body coupled to the pressure mechanism to be substantially freely accelerated over the distance D, i.e., except for the transfer body and possibly the pressure mechanism and/or individual components of the pressure mechanism, substantially no other elements are accelerated along the distance D. Once the pressure mechanism has accelerated the transfer body along the distance D, the transfer body has a defined impulse with which it strikes the contact point, to transfer the impulse or force onto the piston. Said impulse is thus transferred onto the piston and via the piston onto the fluid situated in the pressure chamber, which is thus put under substantial pressure and is expelled from an expelling opening of the pressure chamber at a sharply rising pressure and therefore at a high initial impulse.

A rapid pressure rise for generating a fluid jet dispensed through the expelling opening of the pressure chamber enables the fluid to be accelerated to a sufficiently high velocity that the tip of the jet penetrates into a body, such as through and/or into the skin or another tissue, without a needle being used to inject the fluid. Since the transfer body is accelerated substantially freely over the distance D and strikes a contact point, a relatively high initial impulse or force can be generated, which enables the fluid to be rapidly accelerated and expelled at a velocity which is sufficient for the expelled fluid to be able to penetrate into the body by itself, wherein after a short time period following the relatively high initial impulse, the pressure on the fluid decreases relatively rapidly back to a dispensing pressure which can be lower than the initial pressure, since at this lower pressure level, the fluid can only be introduced into the body and the opening in the body has already been generated by the high initial pressure of the fluid. The accelerated transfer body striking a contact point connected to the piston accordingly generates an impact which causes a pressure spike at the beginning of expelling or injecting the fluid.

In some embodiments, the device of the present invention is preferably designed needle-free, i.e., the body is penetrated by the fluid alone, which exits at high pressure and, due to the high pressure, can generate an entry opening into the body, and penetrates into the body. In principle, however, it is also possible to use the device in combination with a needle or other suitable auxiliary instruments which facilitate or assist injecting or dispensing the fluid.

In some embodiments, the pressure mechanism is designed as a spring mechanism, in particular as an individual spring. Alternatively, it is also possible to provide any pressure mechanism which can dispense gas or a liquid at a high velocity, for example a pressure cartridge or the like. It is also possible to generate the required pressure in other ways, for example, to supply it from an external pressure source, in order to generate the force necessary to accelerate the transfer body.

In one preferred embodiment, a spring mechanism is provided as the pressure mechanism which can be varied with respect to its parameters. Thus, for example, a combination of two or more spring elements can be provided, via which the spring constant of the overall spring mechanism used can be set. This can be achieved by connecting two or more individual spring elements in parallel or in series, as required, in order to obtain a desired spring constant of the resultant overall spring system. Furthermore, the mass of the spring system used for the injection can also be varied, by using a selection of particular individual spring elements. Furthermore, it is also possible to provide a spring body, wherein depending on the desired spring properties, only a defined partial region of the spring body, possibly in combination with other spring elements or partial regions of spring elements, is used.

In some preferred embodiments, the mass and/or the length of the transfer body can be varied. The mass of the transfer body to be accelerated can, for example, be varied by forming the transfer body by means of a plurality of coaxially nested tubular elements, wherein only a portion of the coaxial bodies or all the coaxial bodies are accelerated by a radially extending slaving means which may be connected to the pressure mechanism, in order to generate a desired impulse when striking the contact point, for transferring the force onto the piston, by suitably selecting the mass of the transfer body. The length of the transfer body can be realized by telescopic individual elements which are also coaxial tubular elements which once extended can be latched in a defined position with another element.

It is advantageous to design the piston to be variable with regard to its length and/or mass to be accelerated, wherein it is in principle possible to fall back on the same mechanisms described above for the transfer body, i.e., coaxial elements can, for example, be used to vary the length and/or the mass of the piston to be accelerated.

Generally speaking, designing the transfer body and/or the piston to be variable is not limited to coaxial elements. Rather a number of other combinations, such as for example adjacent or axially adjacent elements, can be used which can as applicable be connected to or separated from the body to be accelerated in order to be able to realize a desired impulse and/or pressure progression of the expelled fluid.

Advantageously, in some embodiments, the distance D between the transfer body and the contact point for transferring the force onto the piston, i.e., the distance D which the transfer body can freely travel in the accelerating phase, is substantially constant when the pressure chamber is filled. If, for example, the contact point for transferring the force or impulse onto the piston is axially offset further towards the expelling opening when a lower fluid volume is to be expelled, then the front end of the transfer body striking the contact point is likewise offset further towards the expelling opening, in order to keep the distance D substantially constant. In this way, a defined initial impulse or pressure of the fluid as it is expelled from the expelling opening of the pressure chamber can be generated, irrespective of the fluid amount to be dispensed, if the force applied via the pressure mechanism is the same. In some embodiments, the force can be set as applicable using a variable spring mechanism. In this respect, it is in particular advantageous, when evacuating or after evacuating the pressure chamber filled with the fluid, to suitably track the transfer body in order to obtain the desired distance D. It is also possible, given an available distance D, to suitably set the pressure mechanism in order to obtain the desired initial impulse or pressure.

In some embodiments, the distance D between the contact point and the transfer body striking the contact point is in the range of 0.1 mm to 10 cm in the initial position, in particular in the range of 1 mm to 8 mm, and in some preferred embodiments, in the range of 2 mm to 6 mm.

In some embodiments, it is advantageous to provide a mechanism to enable the pressure chamber to be filled and/or evacuated only when the expelling opening of the pressure chamber is pointing substantially upwards, in order to prevent an undesired loss of fluid or incomplete evacuation.

Advantageously, the pressure chamber and/or the piston, possibly together with a needle for filling the pressure chamber, and/or other elements of the device are designed as disposable parts, so-called "disposables," in order to be able to rule out the danger of infection when using the device a number of times. In this respect, it is in particular advantageous to configure the expelling mechanism such that when the piston has been inserted, i.e., after the fluid has been displaced from the pressure chamber, it is no longer moved back, such that in practice it is not possible to re-use a pressure chamber which has been used once.

In some embodiments, the device in accordance with the present invention is designed such that the pressure of the expelled fluid rises to a maximum value of 150 to 400 bars, in some preferred embodiments 250 to 400 bars, within a time period of a few milliseconds, e.g., 0.1 to 20 msec, preferably 0.5 to 10 or 1 to 5 msec, or a few microseconds, e.g., 1 to 1000 μsec or 1 to 100 μsec, whereupon the maximum pressure or a high pressure level is maintained for a time period of a few milliseconds, e.g., 0.1 to 20 msec, preferably 0.5 to 10 or 1 to 5 msec, or a few microseconds, e.g., 1 to 1000 μsec or 1 to 100 μsec, and then decreases to a second pressure level of 50 to 150 bars, preferably 80 to 130 bars, within a time period of a few milliseconds, e.g., 0.1 to 20 msec, preferably 0.5 to 10 or 1 to 5 msec, or a few microseconds, e.g., 1 to 1000 μsec or 1 to 100 μsec, during which the dosage to be injected is dispensed. After the dosage to be injected has been dispensed, the pressure of the expelled fluid preferably decreases as rapidly as possible back to zero, in order to keep the wastage volume of non-penetrating fluid as low as possible.

In accordance with one embodiment of a method for injecting a fluid in accordance with the present invention, a force transfer body is substantially freely accelerated along a distance D and then strikes a contact point to generate an initial impulse or pressure to expel a fluid from a pressure chamber.

In some embodiments, the initial impulse or pressure thus generated is substantially constant at a value of approximately 100 to 500 bars, preferably 150 to 400 bars, for a pre-set time period of approximately 0.1 to 5 msec, preferably 0.5 to 2 msec, and decreases to a second pressure level of for example 50 to 150 bars, which is held or gently decreases during a time period determined in accordance with the dosage of fluid to be injected. The pressure then decreases back to zero during a time period of approximately 1 to 500 msec, preferably 100 to 200 msec, and, in some embodiments, approximately 150 msec.

Advantageously, the accelerated masses, in particular of the transfer body and/or the piston, and the properties of the pressure mechanism, e.g., the spring constant or the mass of the spring, are selected or set such that a pre-set pressure progression with a high initial impulse can be realized.

BRIEF DESCRIPTION OF THE DRAWINGS

The invention will now be depicted and described by way of exemplary embodiments as follows.

DETAILED DESCRIPTION

Figure 1:
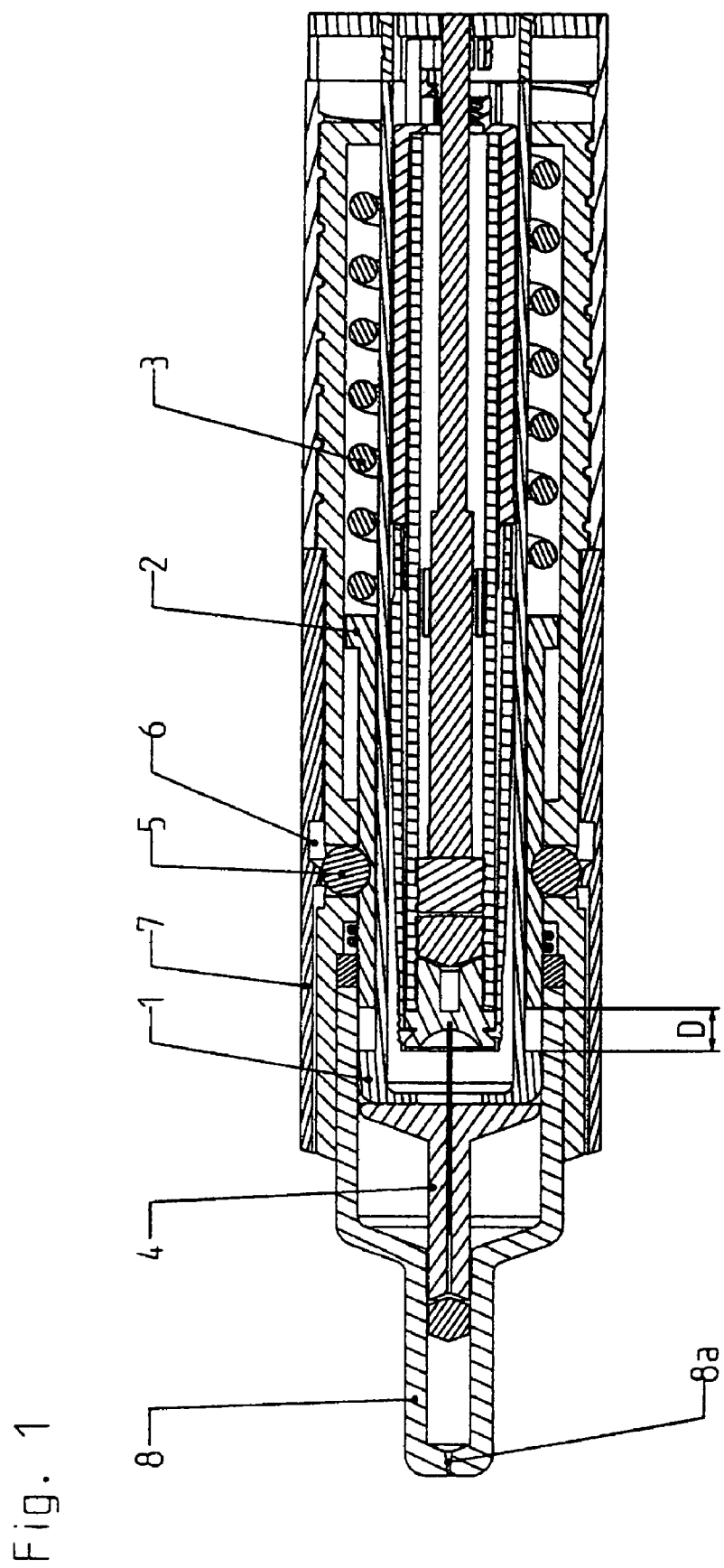
FIG. 1 shows the mechanism of one embodiment of the device in accordance with the present invention.

FIG. 1 shows one embodiment of an injection device comprising a triggering sleeve 7 which can be shifted in the axial direction. Said triggering sleeve 7 can be shifted forwards in the axial direction, i.e., in FIG. 1, to the left, in order to trigger an injection. This motion also pushes the arresting sleeve 2, which serves as a transfer body for an impulse or force, forwards. If the cavities 6 of the triggering sleeve 7 come to rest over the arresting spheres 5, said arresting spheres 5 are pressed radially outwards into the cavities 6 of the triggering sleeve 7 by the force of the spring 3 which, in this embodiment, is formed as a spiral spring. The arresting sleeve 2 is thus released by the arresting spheres 5 and accelerated forwards along the free distance D by the spring force of the injection spring 3, in order—after it has traveled the distance D—to strike the evacuating sleeve 1 and transfer a large initial impulse onto the evacuating sleeve 1 and the nozzle piston 4. This pushes the piston 4 into the pressure chamber 8 filled with a fluid, which outputs the fluid through the exit opening 8a at a rapidly rising high initial pressure.

Figure 2A:
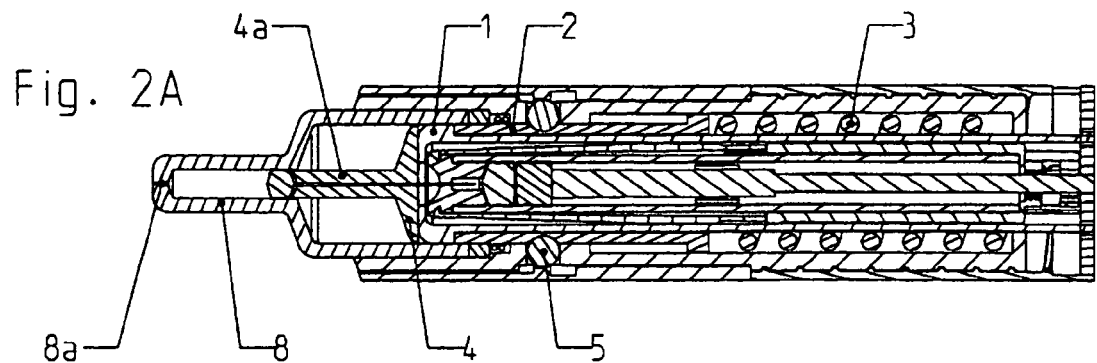
FIGS. 2A to 2D show various operational states of the device shown in FIG. 1.

FIG. 2A shows the initial position of the device shown in FIG. 1, wherein the injection spring 3 is tensed and the arresting sleeve 2 is locked by the arresting spheres 5. The evacuating sleeve 1 abuts the nozzle piston 4.

Figure 2B:
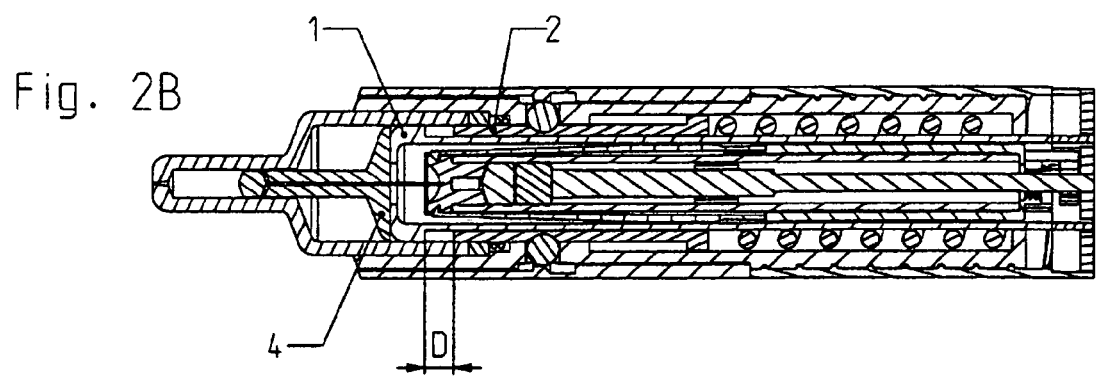

Once the pressure chamber 8 has been filled with a fluid to be expelled via a filling channel 4a running through the nozzle piston 4, the pressure chamber 8 is evacuated, as shown in FIG. 2B. To this end, the evacuating sleeve 1 is shifted forwards in the axial direction, together with the nozzle piston 4, by the distance D, i.e., to the left in the embodiment shown in FIG. 2B.

The distance D for evacuating the pressure chamber 8 can be varied, depending on the dosage of the fluid to be dispensed, the arresting sleeve 2 preferably being tracked such that a constant distance D is substantially maintained. This is not, however, required for the purposes of the invention.

Figure 2C:
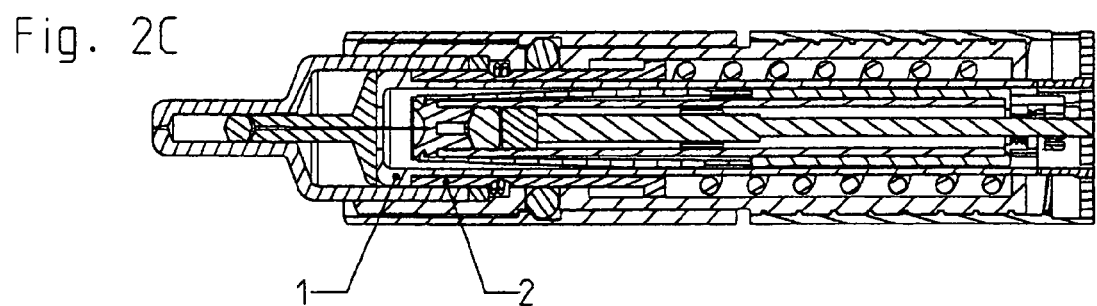

Once the arresting spheres 5 have released the arresting sleeve 2 as described above, the arresting sleeve 2 is accelerated along the distance D by the annular spring 3 and strikes the evacuating sleeve 1 at a relatively high velocity, which transfers a large impulse onto the evacuating sleeve 1 and—via the nozzle piston 4 abutting the evacuating sleeve 1—onto the fluid situated in the pressure chamber 8. This high initial impulse when the arresting sleeve 2 strikes causes a high pressure spike at the beginning of expelling the fluid, i.e., at the beginning of an injection. If the distance D is not kept substantially constant, then a small dosage to be dispensed results in the nozzle piston 4 being shifted further forwards—i.e., in the embodiment shown, to the left—together with the evacuating sleeve 1, which increases the free distance D for accelerating the arresting sleeve 2 using the spring. This increases the accelerating distance D, which likewise increases the transferred initial impulse. In such a case, the injection spring 3 has already dispensed a large portion of its energy to the arresting sleeve 2 when the arresting sleeve 2 strikes the evacuating sleeve 1. FIG. 2C shows the device in accordance with the present invention as the arresting sleeve 2 strikes the evacuating sleeve 1, wherein a high initial impulse is transferred onto the fluid in the pressure chamber 8.

Figure 2D:
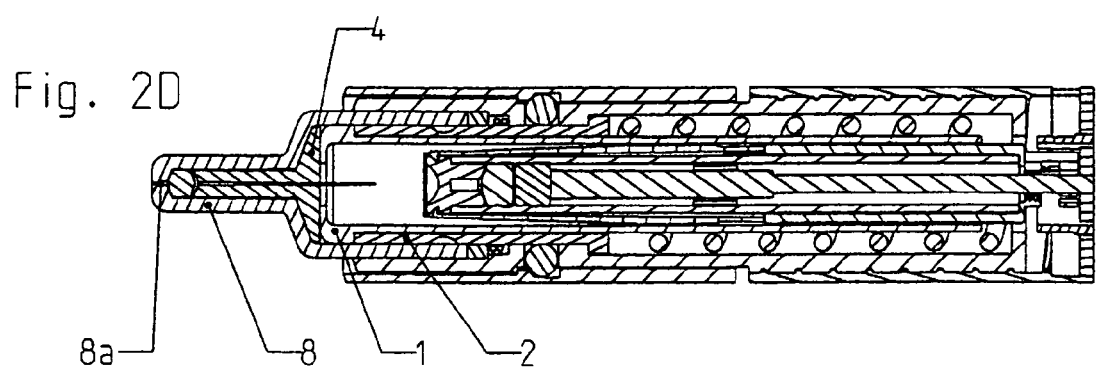

FIG. 2D shows the device in accordance with the present invention after the fluid has been expelled from the pressure chamber 8. Once the arresting sleeve 2 had struck the evacuating sleeve 1, the evacuating sleeve 1 was accelerated together with the nozzle piston 4 and the liquid by the kinetic energy of the arresting sleeve 2 and the residual force of the spring element 3 and output through the expelling opening 8a.

To re-use the device shown, the pressure chamber 8, together with the nozzle piston 4 inserted into the pressure chamber 8, is removed and the spring 3 is tensed again, the arresting sleeve 2 being returned to the position shown in FIG. 2A. A new pressure chamber 8, comprising a nozzle piston 4 which has not yet been inserted, is then attached, whereupon the pressure chamber 8 can be filled with a desired amount of the fluid again from a storage reservoir via the fluid conduit 4a in the nozzle piston 4.

Figure 3:
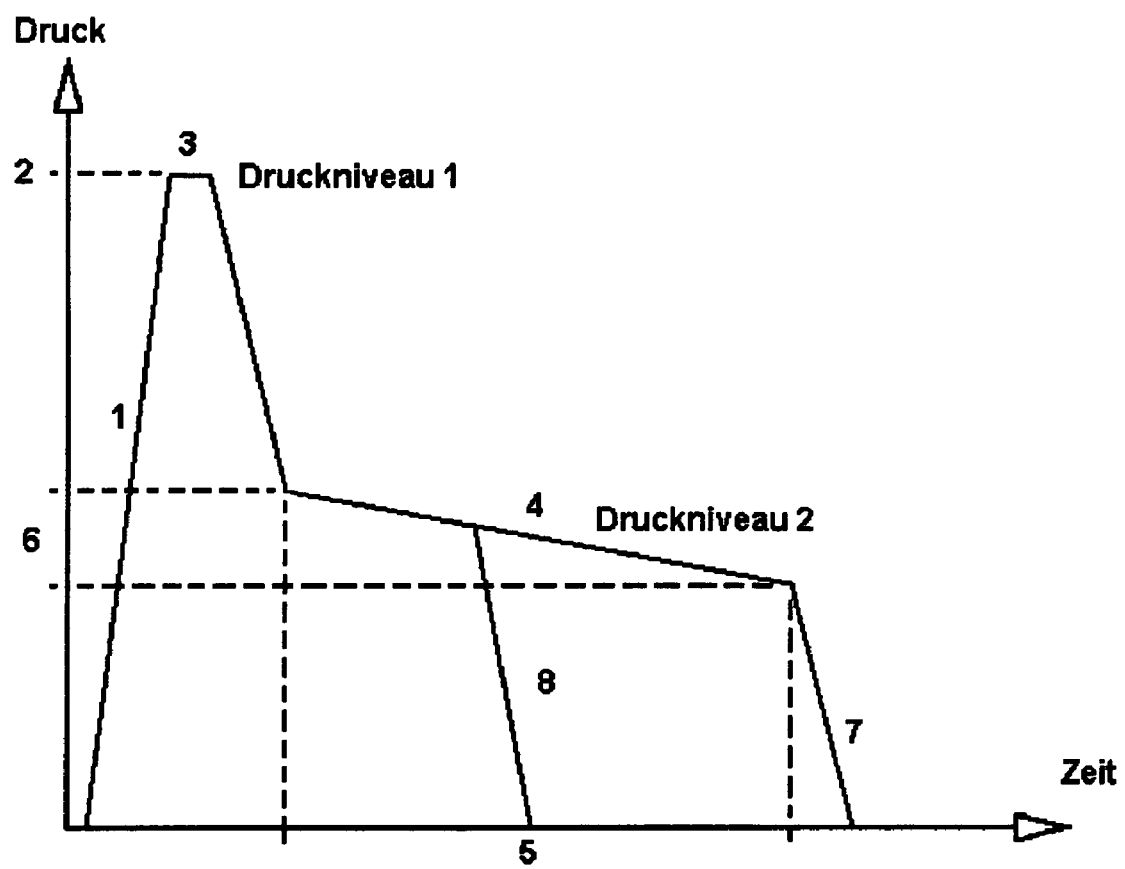
FIG. 3 schematically shows the pressure profile of the dispensed fluid realized by the device shown.

FIG. 3 shows the pressure profile of the fluid dispensed using the device shown in FIGS. 1 and 2. Shortly after the arresting sleeve 2 strikes the evacuating sleeve 1, the pressure of the fluid rises relatively rapidly to the pressure 1, this pressure level 1 being approximately constant for a short time period, enabling the tip of the fluid jet to penetrate into a body, for example into the skin or other tissue. The penetration of the skin and the depth of penetration can be set by the height and duration of the pressure level 1. Once the high initial impulse caused by the arresting sleeve 2 striking the evacuating sleeve 1 has subsided, the pressure level 2 is set which slowly subsides between the pressures 2 and 3 and which must be sufficiently large to ensure that the fluid is transferred out of the pressure chamber 8. The size of the dosage can be determined by the duration of the pressure level 2 and by the mass flow which can for example be set by the size of the expelling opening 8a.

Once the pressure level 2 has been applied for the time period $\Delta t_1$, the pressure decreases relatively rapidly back to zero, when the nozzle piston 4 is inserted substantially completely into the pressure chamber 8. The more rapid the pressure decrease at the end of the pressure profile, the lower the wastage volume of non-penetrating fluid.

If a small dosage of fluid is dispensed, then the time period $\Delta t_2$ during which the pressure level 2 is applied is shorted, as shown in FIG. 3.

Figure 4:
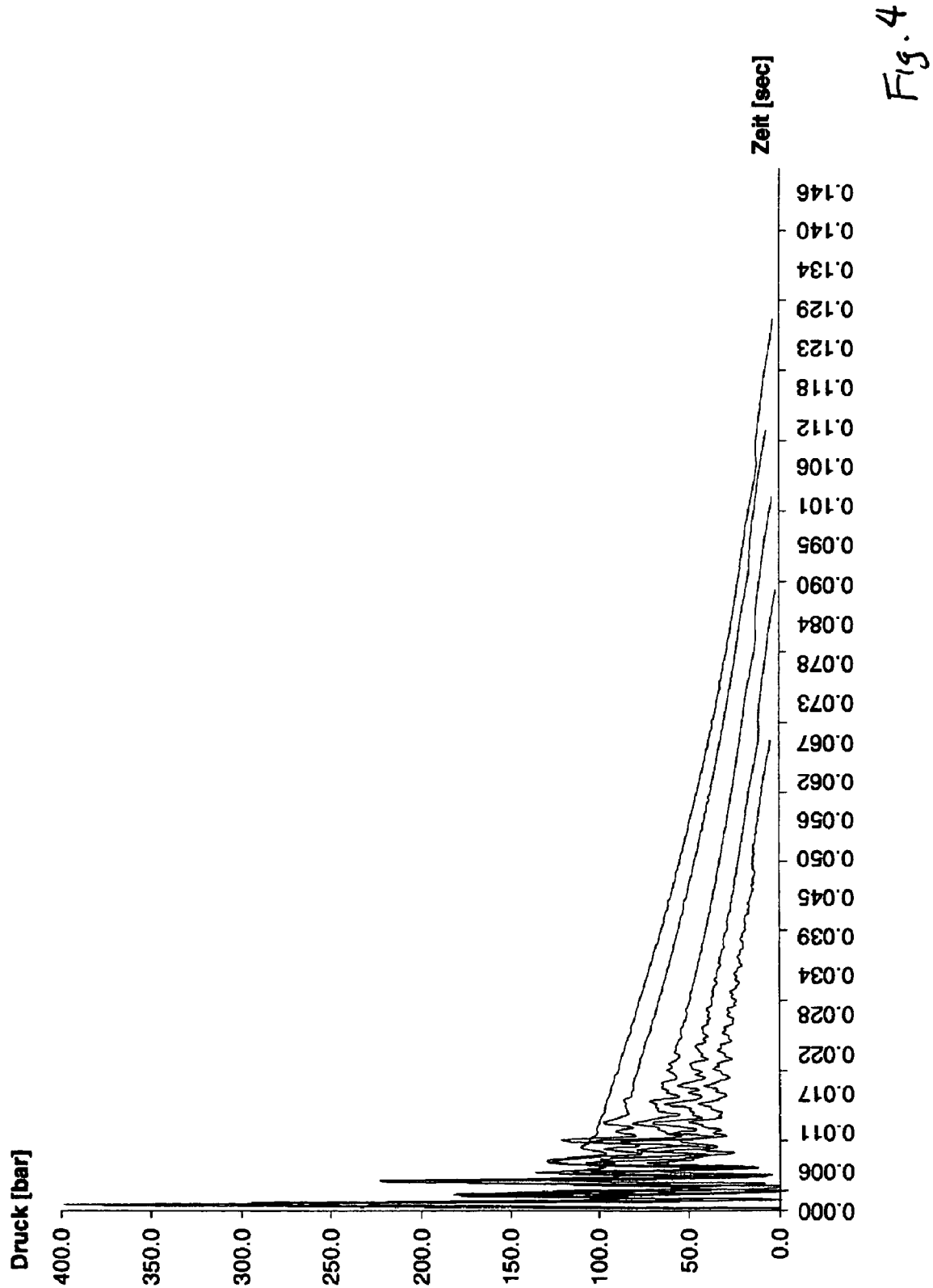
FIG. 4 shows measured pressure progressions of devices in accordance with the present invention.

FIG. 4 shows four measured pressure progressions of devices in accordance with the invention. The pressure progressions which can be read from the diagram in FIG. 4 should be understood as belonging to the invention with respect to their concrete numerical values. Thus, for example, a pressure progression is measured in a first exemplary embodiment of the invention, wherein the pressure of the expelled fluid rises from 0 to approximately 400 bars within the first two to three milliseconds and after a slight oscillation decreases to approximately 100 bars after approximately 6 to 8 milliseconds, and wherein a flat, approximately uniform pressure decrease from 100 bars to a few bars could be measured during the subsequent time period of approximately 120 msec.

By measuring other embodiments, the other pressure progressions shown in FIG. 4 were ascertained, wherein the initial pressures were in some cases significantly below 400 bars, e.g., in the range of 150 to 200 bars, and the pressures set thereafter was in the range of approximately 25 to 100 bars and gradually decreased to a few bars within time periods of approximately 60 to approximately 110 msec.

It can clearly be seen that the initially generated high pressure, as compared to the subsequent gradually subsiding lower pressure, maintains the peak value for a relatively short time period.

Figure 5:
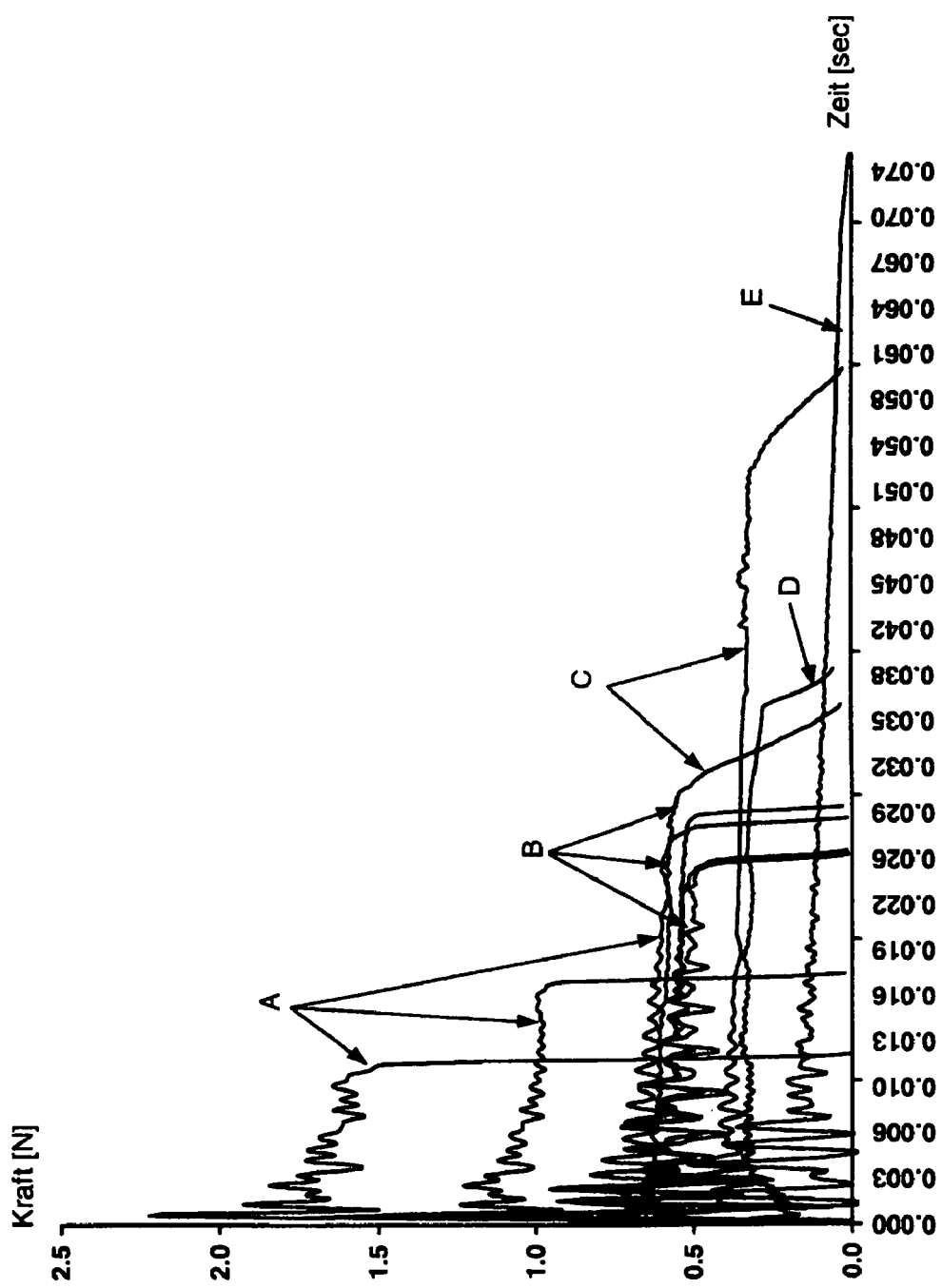
FIG. 5 shows the measured force of devices in accordance with the present invention.

FIG. 5 shows the results of measuring the force for various variants of five types A, B, C, D and E of embodiments in accordance with the invention, when dispensing a dosage of 0.1 mm.

An initial force generated using an injection device in accordance with the present invention can rise to a value of up to 2.3 N within a time period of approximately 1 to 2 msec and then decrease to a force in the range of 1.5 N to 1.9 N, which in a first embodiment is maintained for a time period of approximately 11 msec. Other embodiments of the invention generated lower maximum values for the initial force in the range of approximately 0.5 N to 1.8 N, whereupon the force then set was set to an approximately constant value of approximately 0.2 N to approximately 1.1 N.

Given below, by way of example, are numerical values for suitable pressure or force values in the sense of the present invention, for the schematic diagram shown in FIG. 3. The force relates to a nozzle (jet) diameter of approximately 0.16 mm.

| Pressure level 1 | |
|---|---|
| Maximum value: | 200 to 400 bars (corresponding to approximately 0.5 to 2.5 N, preferably 1 to 2 N) |
| within: | e.g. 0.001 s (should be as short as possible) |
| for: | 0.0005 to 0.005 s, e.g. 0.001 s |
| Pressure level 2 (should be decreasing as flat as possible) | |
| Initial value: | 40 to 200 bars (corresponding to approximately 0.15 to 1.5 N, preferably 0.4 to 0.7 N) |
| End value: | 10 to 200 bars ((corresponding to approximately 0.05 to 1.5 N, preferably 0.4 to 0.7 N) |
| Time: | 0.02 to 0.2 s (depending on size of the dosage) |
| Decrease to zero: | as short as possible, e.g. 0.001 s |

In the foregoing description, embodiments of the present invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device for injecting a substance, comprising:
   a) a pressure chamber for accommodating the substance;
   b) a piston for expelling the substance from said pressure chamber;
   c) a pressure mechanism for generating an expelling force; and
   d) a transfer body coupled to said pressure mechanism, wherein in an initial position said transfer body is arranged at a distance away from a contact point for transferring the expelling force to said piston.

2. The device as set forth in claim 1, wherein said substance is a fluid.

3. The device as set forth in claim 1, wherein said device is a needle-less device.

4. The device as set forth in claim 3, wherein said device is suitable for directly injecting a substance exiting an expelling opening.

5. The device as set forth in claim 1, wherein the pressure mechanism is one of a spring, a pressurized gas and a hydraulic fluid device.

6. The device as set forth in claim 5, wherein the spring has a spring constant and a mass, and wherein at least one of the spring constant and mass can be varied.

7. The device as set forth in claim 1, wherein the transfer body and the piston have a mass, and wherein the mass of the transfer body and piston can be varied.

8. The device as set forth in claim 7, wherein the mass of the transfer body and the piston are varied via mass elements which may be coupled separately.

9. The device as set forth in claim 1, wherein the distance is constant before triggering the pressure mechanism.

10. The device as set forth in claim 9, wherein the distance is constant after evacuating the pressure chamber.

11. The device as set forth in claim 1, wherein the distance is in the range of 0.1 mm to 10 cm.

12. The device as set forth in claim 1, wherein the distance is in the range of 1 mm to 8 mm.

13. The device as set forth in claim 1, wherein the distance is in the range of 2 mm to 5 mm.

14. The device as set forth in claim 1, wherein a locking device is provided which prevents the pressure chamber from being filled and/or evacuated when the expelling opening of the pressure chamber is not held substantially upwards.

15. The device as set forth in claim 1, wherein the pressure chamber and/or the piston are disposable parts coupled to the device.

16. The device as set forth in claim 1, wherein a maximum pressure in the range of 150 to 400 bars and a dispensing pressure in the range of 50 to 150 bars can be generated using the device.

* * * * *